(12) United States Patent
Mann et al.

(10) Patent No.: US 8,117,926 B2
(45) Date of Patent: Feb. 21, 2012

(54) METHOD OF AND EQUIPMENT FOR PREPARING AN ANALYSIS SAMPLE

(75) Inventors: Kari Mann, Espoo (FI); Timo Niitti, Kuopio (FI); Christian Von Alfthan, Espoo (FI); Kari Saloheimo, Espoo (FI)

(73) Assignee: Outotec Oyj, Espoo (FI)

( * ) Notice: Subject to any disclaimer, the term of this patent is extended or adjusted under 35 U.S.C. 154(b) by 367 days.

(21) Appl. No.: 12/445,563

(22) PCT Filed: Oct. 17, 2007

(86) PCT No.: PCT/FI2007/000250
§ 371 (c)(1),
(2), (4) Date: Apr. 14, 2009

(87) PCT Pub. No.: WO2008/049957
PCT Pub. Date: May 2, 2008

(65) Prior Publication Data
US 2010/0101337 A1 Apr. 29, 2010

(30) Foreign Application Priority Data

Oct. 26, 2006 (FI) .................................. 20060944

(51) Int. Cl.
*G01N 1/20* (2006.01)
(52) U.S. Cl. .................................................. 73/863.43
(58) Field of Classification Search ........................ None
See application file for complete search history.

(56) References Cited

U.S. PATENT DOCUMENTS

| 4,822,482 A | 4/1989 | Hollingsworth |
| 5,357,995 A * | 10/1994 | King et al. .................... 137/8 |
| 5,616,831 A | 4/1997 | Ferland et al. |

(Continued)

FOREIGN PATENT DOCUMENTS

DE 3430263 A1 2/1986

(Continued)

OTHER PUBLICATIONS

International Search Report dated Jan. 30, 2008 for International Application No. PCT/FI2007/000250.

*Primary Examiner* — Andre Allen
(74) *Attorney, Agent, or Firm* — Buchana Ingersoll & Rooney PC

(57) ABSTRACT

The invention relates to a method of and equipment for preparing an analysis sample (2) for a continuous on-line analysis. According to the invention, a sample material (5) is taken by means of a sampling arrangement (4) from a material flow (24) that contains solid matter and liquid, whereby the sample material (5) is fed into a chamber (6); a layer of material (10), which contains coarse solid matter, depositing in the lower part of the chamber, and a layer of material (8), which contains liquid and fine solids, being separated from the sample material in the upper part of the chamber, whereby at least part of the material (8), which contains fine solids, is moved to the lower part (9) of the chamber (6), from where the analysis sample (2) that has a higher solids content than the sample material (5) is removed.

27 Claims, 3 Drawing Sheets

U.S. PATENT DOCUMENTS

| | | | |
|---|---|---|---|
| 5,641,894 A * | 6/1997 | Hosokawa | 73/64.56 |
| 7,001,505 B2 * | 2/2006 | Hersh | 210/93 |
| 2002/0065615 A1 | 5/2002 | Gust | |
| 2005/0150841 A1 * | 7/2005 | Ferguson | 210/741 |
| 2008/0134805 A1 * | 6/2008 | Blasco et al. | 73/863.03 |
| 2008/0307902 A1 * | 12/2008 | Von Alfthan et al. | 73/863.21 |
| 2009/0095057 A1 * | 4/2009 | Staats | 73/64.56 |
| 2009/0217778 A1 * | 9/2009 | Booth | 73/863.23 |

FOREIGN PATENT DOCUMENTS

| | | |
|---|---|---|
| DE | 92112633 U1 | 1/1993 |
| DE | 4426599 A1 | 2/1996 |

* cited by examiner

METHOD OF AND EQUIPMENT FOR PREPARING AN ANALYSIS SAMPLE

BACKGROUND

1. Field of the Invention

Disclosed herein is a method of and equipment for preparing, for a continuous on-line analysis, an analysis sample that is formed from a sample material, which is taken from a material flow containing solid matter and liquid.

2. Description of Related Art

In industrial processes that treat and process slurries containing solid matter, there is often a need to regularly and continuously control the process on the basis of the element contents of the solid matter in the slurry. It is well-known to use certain analyzing methods in analyzing slurries that contain solid matter. These include optical analyzing methods, nuclear magnetic resonance, laser emission spectroscopy, and capture gamma spectroscopy as well as methods utilizing X-rays, such as the method based on X-ray fluorescence. In order to optimally observe and control the industrial processes on the basis of such measurement results, samples should be taken continuously from the process flow and immediately analyze them without a delay, which is significant compared with the time constant of the process. Mineral separation processes and processes of the hydrometallurgy field are examples of industrial processes, wherein a real-time analyzing of slurries and liquids are required. Flotation, magnetic and gravitational separation, extraction of metals, cleaning of liquid, as well as electrolytic cleaning and recovery processes represent mineral and hydrometallurgy processes that use real-time analyzers.

One technique commonly used in laboratories for analyzing slurry samples is to filter the slurry and dry and grind the solid matter into a finer form, and to compress the sample into a briquette for each analysis. The briquette thus obtained is further taken to an analyzer. However, as the intention is to analyze fine-grained, powdery samples by a continuous on-line analysis, it is obvious that making the briquette for analyzing the sample is complex and sensitive to damages. When analyzing mineral slurries, it is usually preferable to remove water from the sample before analyzing the same. Dewatering the sample makes the analyzing result more accurate and improves the sensitivity to measurement, when analyzing the sample by a measuring technique based on laser beams or X-rays or neutron activation, for example. Known methods of dewatering mineral slurries include thickening/clarification or filtering, wherein, because of the nature of these methods, however, coarse material separates out from the fines. When preparing the sample directly from the process for the real-time analysis, however, the sample should be representative with respect to its particle size distribution, and the shape and weight of the particles. Hence, it is not preferable to directly apply thickening or filtering to the preparation of the sample for the on-line analysis in the methods mentioned above.

SUMMARY

There remains a need for a method of and equipment for making a representative analysis sample for a continuous on-line analyzer. In particular, there remains a need for a method and equipment specifically to prepare an analysis sample from a sample material that is taken from the process and contains solid matter and liquid, the solids content of the analysis sample being higher than that of the sample material.

Disclosed herein is a method of and equipment for preparing an analysis sample for a continuous on-line analysis, whereby, by means of a sampling arrangement, a suitable amount of sample material is taken for the analysis from a material flow containing fine solids and liquid, and fed into a chamber. A layer of material containing coarse solids deposits in the lower part of the chamber, and a layer of material containing liquid and fine solids is separated from the sample material in the upper part. The solid matter contained in the sample material starts to deposit in the lower part of the chamber so that the coarsest and heaviest part of the solid matter deposits the quickest. In the upper part of the chamber, liquid separates from the sample material, also containing light and fine solid matter that deposits slowly. In order to obtain, from the solid matter, a representative analysis sample that contains a higher solids content than the sample material, according to the invention, at least part of the material containing fine solids is moved to the lower part of the chamber, from where the homogeneous and representative analysis sample, which contains a higher solids content than the sample material, is removed. Flowing through the coarse bed of solids, the fine solid matter adheres to coarse particles. According to the disclosed method, material that contains fine solids is moved to the lower part of the chamber until in the upper part, in addition to the liquid, there is only an insignificant amount of fine solids for the representativeness of the analysis sample.

According to an embodiment characteristic of the invention, the material containing fine solids is moved to the lower part of the chamber by pumping. According to an embodiment, at least one pump, such as a hose pump and at least one channel are connected to the chamber for moving the material, which contains fine solids, to the lower part of the chamber.

According to an embodiment of the invention, a means, such as optical measuring equipment, is connected to the channel for measuring the solids content of the material that contains fine solids. According to an embodiment characteristic of the invention, transferring the material, which contains liquid and fine solids, to the lower part of the chamber is interrupted, when the solids content measured for the material is low enough.

According to an embodiment of the invention, the lower part of the chamber is closed for the time of preparing the analysis sample, and opened to remove the analysis sample by means of a movable closing member connected to the lower part, the closing member being used to open and/or close the discharge gate of the lower part. When needed, the analysis sample is mixed before removing it from the lower part of the chamber. According to an example, wings are connected to the closing member to mix the analysis sample.

According to an embodiment of the invention, a flocculation agent is added to the material that contains fine solids to promote the agglomeration of the solid matter.

According to an embodiment of the invention, the chamber is vibrated by means of a vibrating member that is connected to the chamber to facilitate the exit of the analysis sample.

As disclosed herein, the excess liquid, which is formed in connection with preparing the analysis sample, is removed from the lower part of the chamber and, as necessary, the lower part is rinsed between the formations of the analysis samples.

According to an embodiment of the invention, sample material is taken from the material flow to be processed and analyzed at one stage. According to another embodiment of the invention, the sample material is taken from the material flow to be processed and analyzed at least two stages.

According to an embodiment of the invention, the sample material is taken alternately from more than one points of the process to be processed and analyzed using parallel sampling arrangements.

According to an embodiment of the invention, the cross-sectional area of the lower part of the chamber is smaller than that of the upper part of the chamber. According to another embodiment of the invention, the chamber has a constant cross-sectional area and it is in an inclined position. Hence, it is easier to remove the analysis sample from the lower part of the chamber.

According to an embodiment of the invention, the equipment comprises a means to spray water to remove any froth from the surface of the sample material layer in the chamber.

BRIEF DESCRIPTION OF DRAWINGS

In the following, embodiments of the invention are described in detail with the aid of an example and with reference to the appended drawings, wherein.

DETAILED DESCRIPTION OF SPECIFIC EMBODIMENTS

Figure 1:
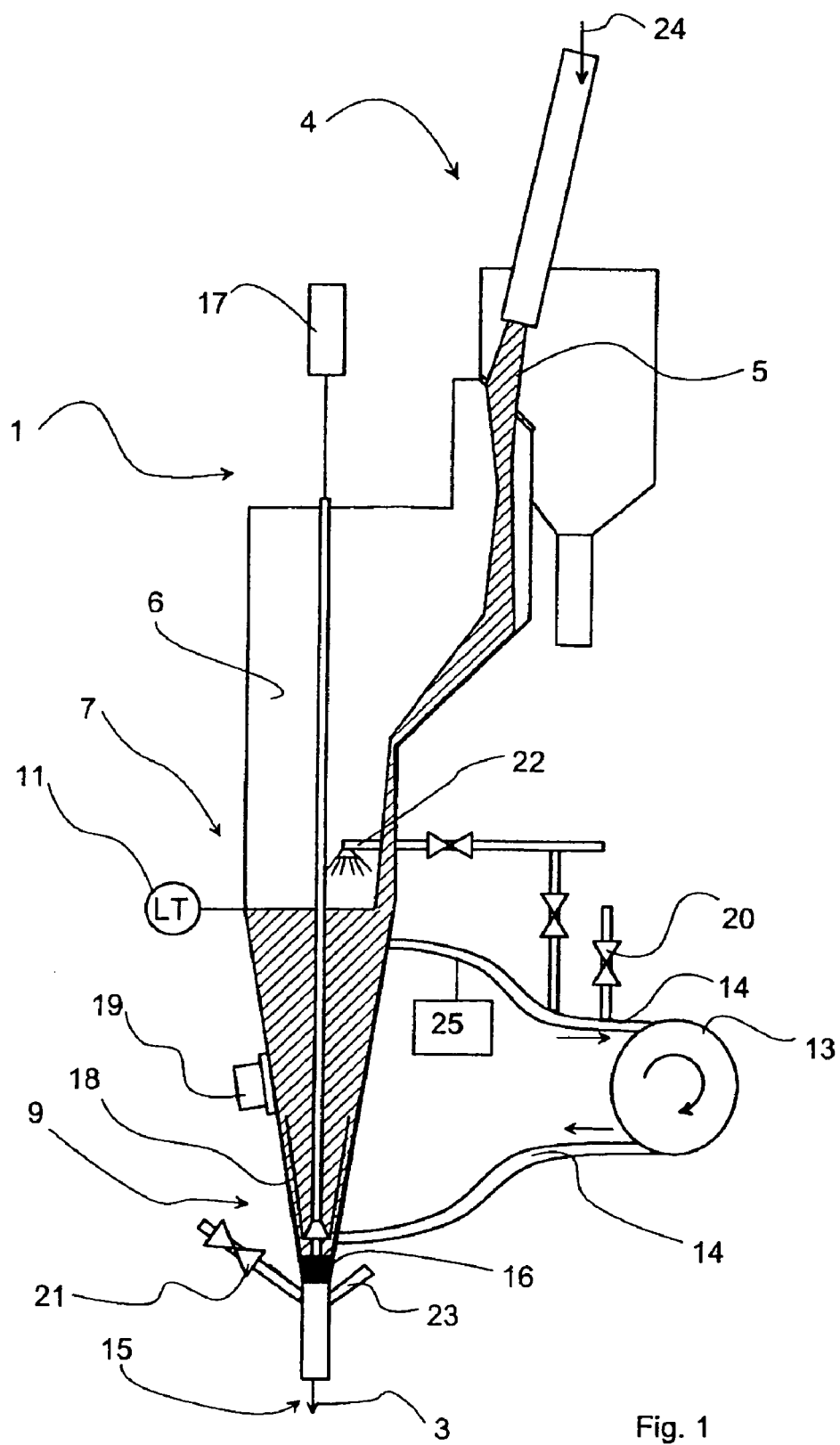
FIG. 1 shows the equipment according to an embodiment of the invention
Figure 2:
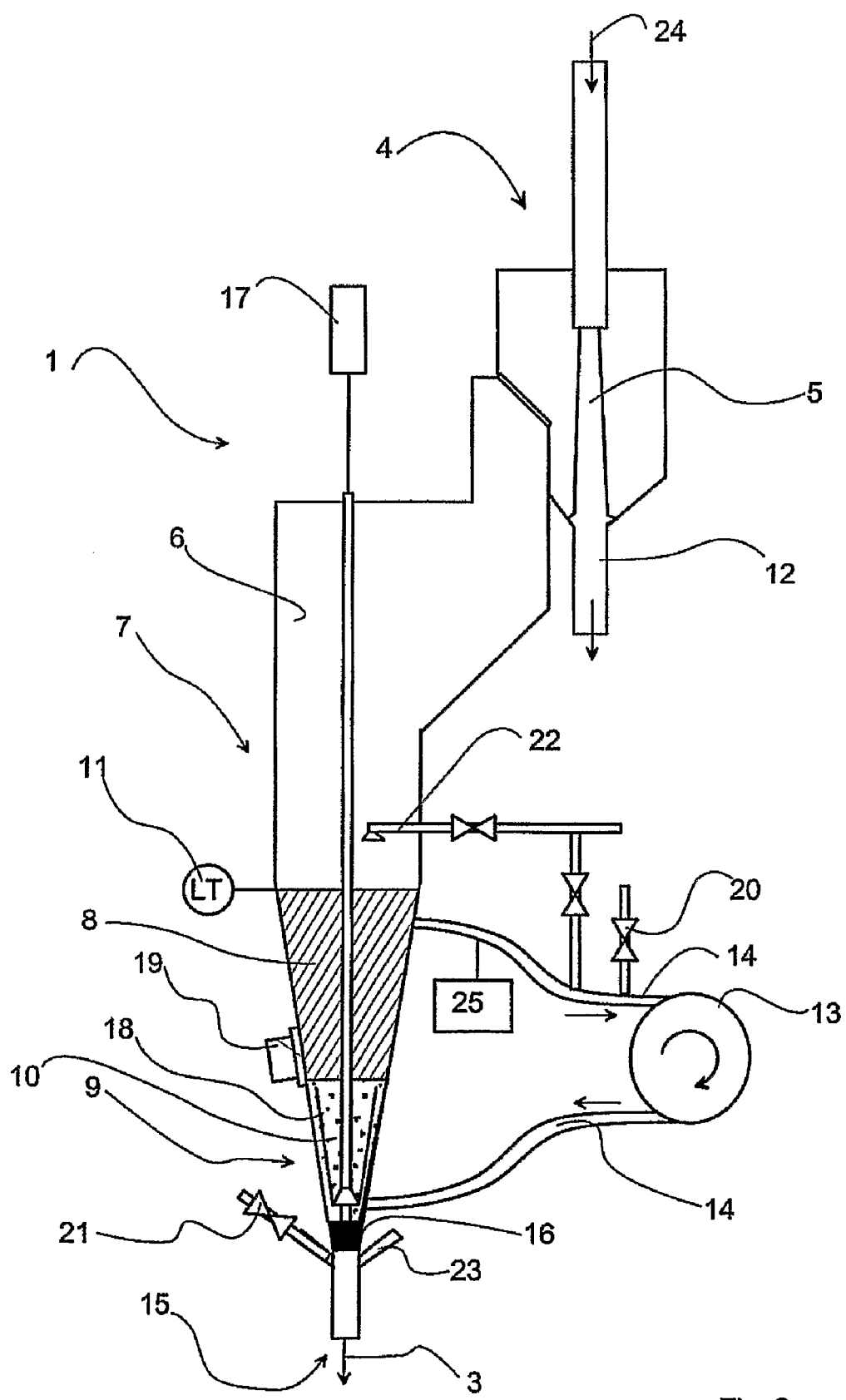
FIG. 2 shows the equipment according to an embodiment of the invention
Figure 3:
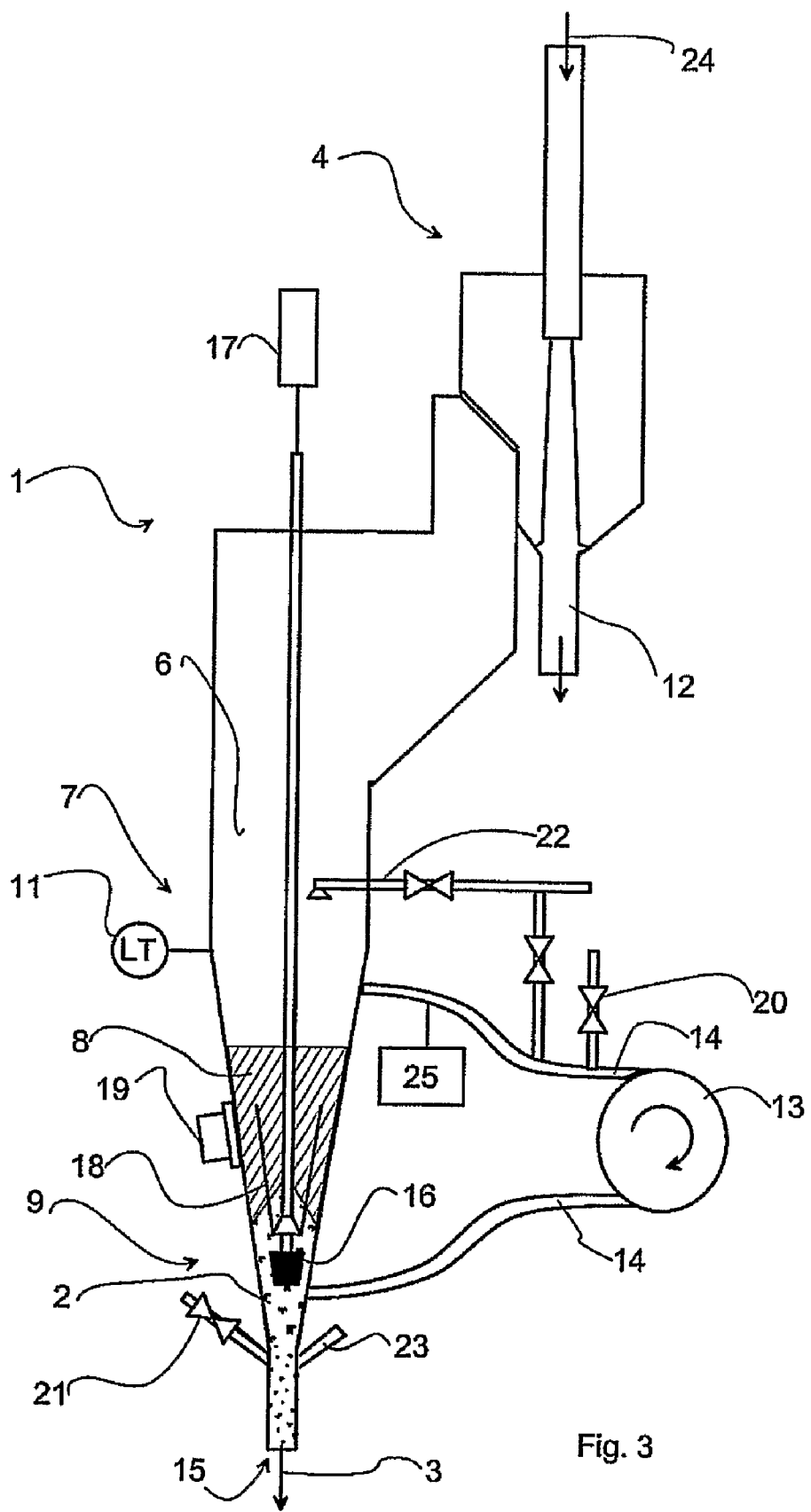
FIG. 3 shows the equipment according to an embodiment of the invention.

FIGS. 1, 2 and 3 illustrate the equipment 1 according to an embodiment of the invention for preparing an analysis sample 2 for a continuous on-line analysis 3. FIG. 1 shows, how a flow of sample material 5 is taken from a material flow 24, which contains fine solids and liquid, by means of a sampling arrangement 4 into a chamber 6 contained in the equipment 1 according to the invention. The material flow 24 is taken from a process, wherein mineral slurry is flowing, for example, by means of any known sampling apparatus. There can also be several material flows 24 and sampling arrangements 4 side by side, whereby the same sample processing chamber 6 and on-line analyzer 3 can be used for measuring several sample flows. The feeding of sample material 5 is terminated, when a desired level is reached and detected with measuring equipment 11 or in another way.

It can be observed from FIG. 2, how a material layer 10, which contains coarse solid matter that deposits quickly, is formed in the lower part 9 of the chamber 6, and, in the upper part 7, a material layer 8 remains, containing liquid and fine solid matter that slowly descends from the sample material. When no sample material 5 is fed to be prepared in the chamber, it can be returned back to the process as a return flow 12. As shown in FIGS. 2 and 3, according to an embodiment of the invention, at least part of the liquid and the material layer 8 that contains fine solids is transferred to the lower part 9 of the chamber 6, whereby, when flowing along with the liquid through the coarse material layer 10, the finer solid particles adhere to the coarser particles and, possibly under the effect of the flocculation agent that is fed, combine or flocculate into larger particles. In that case, it is easier for the finer solid matter particles to remain in the spaces between the granules of the coarser material in the lower part of the chamber 6, which is necessary in order to prepare a representative sample material. In this way, a desired analysis sample 2 containing a higher solids content can be formed. A pump 13, such as a hose pump, is connected to the chamber 6, pumping the liquid 8 containing fine solids, which is situated in the upper part 7 of the chamber, to the lower part 9 of the chamber. The pump moves the material 8 into a channel 14, such as a hose, by means of which the material is moved to the lower part 9 of the chamber. After this, the pump is stopped and the representative analysis sample 2, which is formed in the lower part of the chamber, is ready to be removed through the discharge gate 15, as shown by FIG. 3. In the analysis sample 2, there is a considerably larger amount of solid matter, preferably 80% by weight, for example, if the sample material contained 20% by weight of solid matter. The sample material 2 is conducted from the lower part of the chamber to be analyzed in the analyzer 3.

If the sample material 5 contains froth, a water jet is sprayed on its surface by means of a spraying member 22 that is placed in connection with the chamber 6, to remove the layer of froth. The chamber 6 has a shape of a downwards convergent, pointed cone or the like, for example, so that the analysis sample 2 can preferably be removed from the lower part 9 of the chamber 6. After the sample preparation, the analysis sample 2 that contains a higher solids content than the sample material 5 is removed in the manner shown by FIG. 3.

The discharge gate 15 in the lower part 9 of the chamber 6 can be closed mechanically, for example, by means of a closing member 16, such as a rubber plug, which is pneumatically movable in the vertical direction. The opening and closing mechanism 17, which is connected to the plug, has wings 18 connected thereto, mixing and moving the completed analysis sample 2, while the plug 16 is raised. A vibrator 19 is connected to the chamber 6, helping the analysis sample 2 move downwards in the chamber and, hence, also in removing the analysis sample. When needed, a flocculation agent 20 is added to the material flow 8, which is moved from the upper part of the chamber to its lower part and which contains fine solid matter, to promote agglomeration. In connection with the discharge gate 15 of the lower part 9 of the chamber 6, there are also nozzles 21 for spraying a cleaning liquid to the lower part of the chamber between the preparations of analysis batches. The fine material is pumped until the upper part of the sample has clarified sufficiently, and the coarse analysis sample 2 has formed in the lower part of the chamber. The excess liquid that is formed in the preparation of the analysis sample 2 can be removed through a discharge unit 23 that is placed in the lower part of the chamber. The data that is analyzed from the analysis sample 2 can be further utilized in the process control and optimization.

A means 25, such as equipment for measuring optical turbidity, is connected to a channel 14 for measuring the solids content of the material 8 that contains fine solids. The transfer of the material 8, which contains liquid and fine solids, to the lower part 9 of the chamber 6 is interrupted, when the solids content measured for the material 8 is low enough.

The invention is not exclusively limited to the embodiments described above, but various modifications are viable within the inventive idea defined by the claims.

The invention claimed is:

1. A method of preparing an analysis sample for a continuous on-line analysis,
    wherein a sample material is taken by means of a sampling arrangement from a material flow that contains solid matter and liquid,
    wherein the sample material is fed into a chamber,
    a layer of material that contains coarse solid matter depositing in the lower part of the chamber, and a layer of material that contains liquid and fine solid matter separating from the sample material in the upper part of the chamber, wherein at least part of the material that contains fine solids is moved to the lower part of the chamber, from where the analysis sample that contains a higher solids content than the sample material is removed.

2. A method according to claim 1, wherein material containing fine solid matter is moved to the lower part of the chamber, until the analysis sample is formed.

3. A method according to claim 1 wherein the material containing fine solid matter is moved to the lower part of the chamber by pumping.

4. A method according to claim 1, wherein the lower part of the chamber is closed for the time of preparing the analysis sample.

5. A method according to claim 1, wherein the transfer of the material, which contains liquid and fine solids, to the lower part of the chamber is interrupted, when the solids content measured for the material is low enough.

6. A method according to claim 1, wherein a flocculation agent is added to the material, which contains fine solids, to promote the agglomeration of the solid matter.

7. A method according to any of claim 1, wherein the analysis sample is mixed before it is removed from the lower part of the chamber.

8. A method according to any of claim 1, wherein the chamber is vibrated to facilitate the exit of the analysis sample.

9. A method according to any of claim 1, wherein the lower part of the chamber is opened to remove the analysis sample.

10. A method according to any of claim 1, wherein the excess liquid that is formed in the preparation of the analysis sample is removed from the lower part of the chamber.

11. A method according to claim 1, wherein sample material is taken from the material flow to be processed and analyzed at one stage.

12. A method according to claim 1, wherein sample material is taken from the material flow to be processed and analyzed at least two stages.

13. A method according to claim 1, wherein sample material is taken alternately from more than one points of the process to be processed and analyzed.

14. Equipment for preparing an analysis sample for a continuous on-line analysis, wherein a sample material is taken by means of a sampling arrangement from a material flow that contains solid matter and liquid, to be processed by the equipment, comprising at least a chamber, which the sample material can be fed into, the upper part of the chamber containing a layer of material that contains fine solids from the sample material, and its lower part containing a layer of material that contains coarse material, wherein the equipment comprises a means for transferring at least part of the material containing fine solids to the lower part of the chamber, and a means for removing the analysis sample, which contains a higher solids content than the sample material, from the lower part of the chamber.

15. Equipment according to claim 14, wherein at least one pump and at least one channel are connected to the chamber for moving the material that contains fine solids to the lower part of the chamber.

16. Equipment according to claim 15, wherein the pump is a hose pump.

17. Equipment according to claim 15, wherein a means is connected to the channel for measuring the solids content of the material that contains fine solids.

18. Equipment according to claim 17, wherein means for measuring the solids content contain optical measurement equipment.

19. Equipment according to claim 14, wherein the cross-sectional area of the lower part of the chamber is smaller than the cross-sectional area of the upper part of the chamber.

20. Equipment according to claim 14, wherein the cross-sectional area of the chamber is constant and it is in an inclined position.

21. Equipment according to any of claim 14, wherein the equipment comprises a means for spraying water to remove any froth from the surface of the sample material layer in the chamber.

22. Equipment according to any of claim 14, wherein the equipment comprises a means for adding a flocculation agent to promote the agglomeration of the material that contains fine solids.

23. Equipment according to claim 14, wherein a vibrator is connected to the chamber to facilitate the exit of the analysis sample.

24. Equipment according to claim 14, wherein, in the lower part of the chamber, there is provided a movable closing member for opening and/or closing the discharge gate of the lower part.

25. Equipment according to claim 24, wherein wings are connected to the closing member for mixing the analysis sample.

26. Equipment according to claim 14, wherein, in the lower part of the chamber, there is a means for rinsing the same after removing the analysis sample.

27. Equipment according to claim 14, wherein sample flows from more than one process point can be fed into the same equipment by using parallel sampling arrangements.

* * * * *